United States Patent [19]

Wasson

[11] 4,011,217

[45] Mar. 8, 1977

[54] 4-(3-AMINO-2-ACYLOXYPROPOXY)-1,2,5-THIADIAZOLE COMPOUNDS

[75] Inventor: Burton Kendall Wasson, Valois, Canada

[73] Assignee: Merck Sharp & Dohme (I.A.) Corporation, Rahway, N.J.

[22] Filed: Feb. 26, 1975

[21] Appl. No.: 553,186

Related U.S. Application Data

[62] Division of Ser. No. 352,765, April 19, 1973, Pat. No. 3,891,639.

[52] U.S. Cl. .................... 260/247.1 H; 260/268 H; 260/302 D
[51] Int. Cl.² ............. C07D 285/10; C07D 295/12
[58] Field of Search ........ 260/247.1, 302 D, 268 H

[56] References Cited
UNITED STATES PATENTS

| | | | |
|---|---|---|---|
| 3,655,663 | 4/1972 | Wasson | 260/247.1 H |
| 3,657,237 | 4/1972 | Weinstock et al. | 260/247.1 H |
| 3,729,469 | 4/1973 | Wasson | 260/247.1 H |

*Primary Examiner*—Anton H. Sutto
*Assistant Examiner*—Michael Shippen
*Attorney, Agent, or Firm*—J. Jerome Behan; Daniel T. Szura

[57] ABSTRACT

4-[3-(Substituted amino)-2-acyloxypropoxy]-1,2,5-thiadiazole compounds, optionally substituted in the 3-position of the thiadiazole nucleus which exhibit β-adrenergic blocking properties and thus are useful in the management of angina pectoris are described. The products are prepared by reaction of a 4-[3-(substituted amino)-2-hydroxypropoxy]-1,2,5-thiadiazole with the appropriate anhydride. The reaction is run under acidic conditions when the amino nitrogen is protonated.

2 Claims, No Drawings

4-(3-AMINO-2-ACYLOXYPROPOXY)-1,2,5-THIADIAZOLE COMPOUNDS

This is a division of application Ser. No. 352,765 filed Apr. 19, 1973, issued June 24, 1975 as U.S. Pat. No. 3,891,639.

This invention is concerned with 4-[3-(substituted amino)-2-acyloxypropoxy]-1,2,5-thiadiazole compounds which are optionally substituted in the 3-position of the thiadiazole nucleus. These compounds exhibit β-adrenergic blocking properties and have the marked advantages of having a long duration of action and being effective at very low dosage levels. Of particular interest are the 1,2,5-thiadiazole compounds having attached to the 4-position carbon a 3-(substituted amino)-2-hydroxypropoxy group wherein the hydroxy group is present in the form of an ester group. The compounds, particularly when additionally substituted in the 3-position of the 1,2,5-thiadiazole nucleus, exhibit especially desirable β-adrenergic blocking properties.

The novel β-adrenergic blocking agents of this invention have the following structure wherein the atoms of the thiadiazole nucleus have been numbered and all product identification in the specification and claims shall be in accordance therewith:

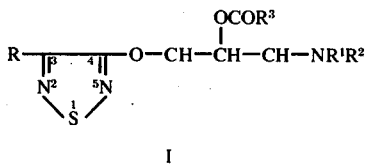

I and pharmacologically acceptable salts thereof, wherein R represents (1) hydrogen, (2) halogen, preferably chloro or bromo, (3) lower alkyl having from 1 to 5 carbon atoms and either a straight or branched chain such as methyl, ethyl, propyl, isopropyl, butyl, iso-, secondary- or tert-butyl and amyl including all of its branched chain configurations, (4) a lower alkoxy having from 1 to 5 carbon atoms and being either a straight or branched chain and including methoxy, ethoxy, propoxy, isopropoxy, butoxy, and pentoxy, the latter groups existing in either straight or branched configuration, (5) N—$C_{1-5}$ alkylcarbamoyl, (6) phenyl, (7) phenyl-$C_{1-5}$ alkyl, (8) morpholino, (9) piperidino, (10) hydroxypiperidino, and (11) N-lower alkyl-piperidino; $R^3$ is selected from a mono- or polysubstituted lower alkyl wherein the alkyl group contains from 2 to 6 carbons and the substituent groups are selected from halogen, preferably chloro, a phenyl, phenoxy, carboxy or ester thereof; $R^1$ represents hydrogen, lower alkyl having a straight or branched chain containing from 1 to 5 carbons, and lower alkanoyl having from 2 to 6 carbons; $R^2$ represents (1) a straight or branched chain alkyl having from 1 up to about 10 carbons but preferably a branched chain alkyl having from 3 to 6 carbons such as isopropyl, tert-butyl, 2,2-dimethylpropyl and the like, optionally being substituted with a hydroxy group, (2), an alkenyl or alkynyl having preferably from 2 to 6 carbons, such as allyl, butynyl, propargyl and the like; and when $R^1$ and $R^2$ separately represent lower alkyl or lower alkenyl they can be joined together either directly or through an oxygen or nitrogen to form a 4 to 6 membered ring with the nitrogen to which they are attached to form, for example, the pyrrolidyl, piperidino, morpholino, and the like.

Suitable pharmacologically acceptable salts of product I are acid addition salts derived from inorganic acids, for example, hydrochlorides, hydrobromides, phosphates or sulfates or salts derived from organic acids, for example, oxalates, lactates, malates, maleates, formates, acetates, succinates, tartrates, salicylates, citrates, phenylacetates, benzoates, p-toluenesulfonates and other salts such as those that provide relatively insoluble products that afford a slow release of the active material, for example, a 1,1′-methylene-bis-(2-hydroxy-3-naphthoate) and the like.

The novel 4-[3-(substituted amino)-2-acyloxypropoxy]-1,2,5-thiadiazole compounds, structure I, as well as their intermediates which contain one asymmetric carbon atom in the propylene chain will be obtained as racemic compounds which can be separated into optically active isomers by known methods, for example, by forming a salt with an optically active acid, many of which are known to those skilled in the art, such as optically active tartaric, mandelic, cholic, 0,0-di-p-toluoyl tartaric, 0,0-dibenzoyl tartaric acids, or other acids conventionally employed for this purpose. Ideally the optically active products are prepared by acylation of the optically active starting substance. The claims therefore will be understood to embrace the products in the form of racemic compounds as well as in the form of the optically active isomers where appropriate.

The clinical application of β-adrenergic blocking agents are well known to physicians. One use for the novel products of this invention, which constitutes the best mode for use of the products known to applicant at this time, is for the control of tachycardia that may be drug induced (as by isoproterenol) or brought about by physiological conditions. In view of the considerable amount of literature that has accumulated concerning the use of β-adrenergic blocking agents, physicians would employ the products of this invention in any of the known conditions where a short-acting or long-acting agent is needed, such as in the management of angina pectoris.

The products can be prepared in pharmaceutical formulations suitable for oral or parenteral administration preferably in the form of tablets, solutions, suspensions and emulsions. The 1,2,5-thiadiazoles can be formulated in the form of the free base or in the form of their salts in conjunction or admixture with organic and/or inorganic solid or liquid pharmaceutical excipients. No special problems are involved in preparing suitable formulations of these products and methods generally employed for this purpose, which are known to those skilled in this art, are entirely suitable. If desired the compounds can be administered along with or formulated together with other active ingredients. Dosage units of from about 2 mg. to 10 mg. can be provided for the symptomatic adjustment of dosage by the physician depending upon the age and condition of the patient.

The novel thiadiazole products I of this invention can be prepared by the reaction of 4-[-3-(substituted amino)-2-hydroxypropoxy]-1,2,5-thiadiazole with the desired acid anhydride or chloride at ambient temperature or with brief warming up to about 100° C. whereupon a good yield of the desired product I is formed. When $R^1$ is the starting substance is hydrogen and should it not be desired to introduce an acyl substituent on the nitrogen, the reaction then is carried out under acidic conditions, using preferably an aliphatic acid suitably acetic acid.

The following examples will illustrate representative products of this invention prepared by the above described procedure. The following examples, however, are not to be considered as limiting the preparation of any particular compound to the method described in the example as the examples are provided solely as to illustrate the best mode currently known to applicant for the preparation of the novel thiadiazoles of this invention.

EXAMPLE 1

3-Morpholino-4-(3-tert-butylamino-2-succinyloxypropoxy)-1,2,5-thiadiazole hydrogen maleate To a solution of 3-morpholino-4-(3-tert-butylamino-2-hydroxypropoxy)-1,2,5-thiadiazole hydrogen maleate (8.64 g., 0.02 mole) in acetic acid (40 ml.) is added succinic acid anhydride (4.01 g., 0.04 mole). The reaction mixture is stirred at ambient temperature overnight. Ether (200 ml.) then is added and stirring continued for an additional half hour. The crystals formed are removed by filtration with suction, washed with ether and dried under suction providing a 59% yield of acylated product, m.p. 128°–132° C.

EXAMPLE 2

S-(−)-3-Morpholino-4-(3-tert-butylamino-2-succinyloxypropoxy)-1,2,5-thiadiazole hydrogen maleate This product is prepared as described above by replacing the 3-morpholino-4-(3-tert-butylamino-2-hydroxypropoxy)-1,2,5-thiadiazole hydrogen maleate by an equivalent quantity of the optically active isomer, S-(−)-3-morpholino-4-(3-tert-butylamino-2-hydroxypropoxy)-1,2,5-thiadiazole hydrogen maleate.

The following table identifies other products prepared by substantially the same procedure described in Example 1, but replacing the reactants by equivalent quantities of the thiadiaoloxypropanolamine and acylating agent identified in the table. The variables R, $R^1$, $R^2$ and $R^3$ in the reactants A and B are carried over unchanged to the end product I. The racemic mixture of reactant A is employed unless the sinister isomer is indicated by preceding the identification of R by the letter S. The end products will be racemic or sinister depending upon the reactant A employed.

TABLE I $$R-\underset{\underset{S}{N\diagdown\diagup N}}{\underset{\parallel\quad\parallel}{\boxed{\phantom{xx}}}}-O-CH_2-\underset{\underset{OH}{|}}{CH}-CH_2-NR^1R^2 \cdot HO_2C-CH=CH-CO_2H + (R^3CO)_2O \longrightarrow$$

$$\qquad\qquad A \qquad\qquad\qquad\qquad\qquad\qquad B$$

$$R-\underset{\underset{S}{N\diagdown\diagup N}}{\underset{\parallel\quad\parallel}{\boxed{\phantom{xx}}}}-OCH_2-\underset{\underset{OCOR^3}{|}}{CH}-CH_2NR^1R^2 \cdot HO_2C-CH=CH-CO_2H$$

$$\qquad\qquad C$$

| R | $R^1$ | $R^2$ | $R^3$ |
|---|---|---|---|
| ethoxy | H | 3-(3,3-dimethylpropargyl) | 2-carboxyethyl |
| hydrogen | H | 2-(2,2-dimethylethanol) | benzyl |
| ethyl | H | 2-(2,2-dimethylethanol) | phenoxymethyl |
| hydrogen | diethylenether | | 3-carboxypropyl |
| ethoxy | diethylenether | | dichloromethyl |
| morpholino | H | isopropyl | 2-carboxyethyl |
| N-t.-butylcarbamoyl | H | t.-butyl | 2-carboxyethyl |
| N-isopropylcarbamoyl | H | isopropyl | benzyl |
| piperidino | H | t.-butyl | 2-carboxyethyl |
| 4-methylpiperazinyl | H | t.-butyl | dichloromethyl |
| 4-hydroxypiperidino | H | t.-butyl | 2-carboxyethyl |
| phenyl | H | t.-butyl | 2-carboxyethyl |
| phenyl | H | isopropyl | benzyl |
| piperidino | H | isopropyl | 2-carboxyethylene |

By replacing the hydrogen maleate as the salt forming acid of the starting substances employed in Examples 1, 2 and the reactants in Table I by an acid addition salt derived from an inorganic acid, for example, hydrochloride, hydrobromide, phosphate or sulfates or salts derived from an organic acid, for example, oxalate, lactate, maleate, formate, acetate, succinate, tartrate, salicylate, citrate, phenylacetate, benzoate or p-toluenesulfonate, the corresponding acid addition salt of product I is formed.

What is claimed is:

1. A racemic product or an optically active isomer thereof having the structure

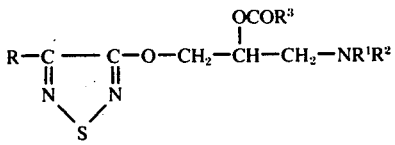

or an acid addition salt thereof wherein R represents hydrogen, chloro, lower alkyl, lower alkoxy, phenyl, benzyl, N-lower alkylcarbamoyl, piperazinyl, N-lower alkylpiperazinyl; $R^1$ represents hydrogen and $C_{1-5}$ alkyl; $R^2$ represents $C_{1-10}$ alkyl, hydroxy $C_{1-10}$ alkyl, lower alkenyl, lower alkynyl; the radical $NR^1R^2$ can represent morpholino; and $R^3$ represents a mono- or polysubstituted lower alkyl wherein the alkyl group contains from 2 to 6 carbons and the substituent groups are selected from halogen, a phenyl, phenoxy or carboxy.

2. A sinister isomer of the product claimed in claim 1.

* * * * *